United States Patent
Kim et al.

(10) Patent No.: US 10,872,604 B2
(45) Date of Patent: Dec. 22, 2020

(54) USER EXPERIENCE EVALUATION

(71) Applicant: QUALCOMM Incorporated, San Diego, CA (US)

(72) Inventors: Lae-Hoon Kim, San Diego, CA (US); Yinyi Guo, San Diego, CA (US); Ravi Choudhary, San Diego, CA (US); Sunkuk Moon, San Diego, CA (US); Erik Visser, San Diego, CA (US); Fatemeh Saki, San Diego, CA (US)

(73) Assignee: Qualcomm Incorporated, San Diego, CA (US)

(*) Notice: Subject to any disclaimer, the term of this patent is extended or adjusted under 35 U.S.C. 154(b) by 232 days.

(21) Appl. No.: 15/982,851

(22) Filed: May 17, 2018

(65) Prior Publication Data
US 2019/0355351 A1    Nov. 21, 2019

(51) Int. Cl.
| | |
|---|---|
| *G10L 15/22* | (2006.01) |
| *G06F 3/0484* | (2013.01) |
| *G06F 3/16* | (2006.01) |
| *G10L 15/18* | (2013.01) |
| *G10L 25/63* | (2013.01) |
| *G10L 15/08* | (2006.01) |

(52) U.S. Cl.
CPC ............ *G10L 15/22* (2013.01); *G06F 3/0484* (2013.01); *G06F 3/167* (2013.01); *G10L 15/1807* (2013.01); *G10L 25/63* (2013.01); *G10L 2015/088* (2013.01); *G10L 2015/223* (2013.01)

(58) Field of Classification Search
USPC ..................................... 704/257, 255, 1–504
See application file for complete search history.

(56) References Cited

U.S. PATENT DOCUMENTS

| | | | | |
|---|---|---|---|---|
| 8,634,852 | B2* | 1/2014 | Farmer | H04M 1/6058 |
| | | | | 455/456.1 |
| 9,092,394 | B2  | 7/2015 | Dokor et al. | |
| 9,109,917 | B2* | 8/2015 | Foster | G06F 3/167 |
| 9,123,341 | B2  | 9/2015 | Weng et al. | |
| 9,286,029 | B2* | 3/2016 | Raux | G06F 3/167 |
| 9,462,115 | B2* | 10/2016 | Rand | H04R 1/1041 |
| 9,671,243 | B2* | 6/2017 | Stein | G01C 21/3602 |

(Continued)

FOREIGN PATENT DOCUMENTS

JP    2010128015 A    6/2010

OTHER PUBLICATIONS

International Search Report and Written Opinion—PCT/US2019/031706—ISA/EPO—dated Jun. 28, 2019.

(Continued)

*Primary Examiner* — Marcus T Riley
(74) *Attorney, Agent, or Firm* — Moore IP

(57) ABSTRACT

A device includes a memory configured to store a user experience evaluation unit. A processor is configured to receive a first user input corresponding to a user command to initiate a particular task, the first user input received via a first sensor. The processor is configured to, after receiving the first user input, receive one or more subsequent user inputs, the one or subsequent user inputs including a second user input received via a second sensor. The processor is configured to initiate a remedial action in response to determining, based on the user experience evaluation unit, that the one or more subsequent user inputs correspond to a negative user experience.

30 Claims, 6 Drawing Sheets

(56) References Cited

U.S. PATENT DOCUMENTS

| | | | |
|---|---|---|---|
| 9,677,901 B2* | 6/2017 | Yamamoto | A61H 3/06 |
| 10,024,667 B2* | 7/2018 | Moore | G01C 21/165 |
| 2001/0053956 A1* | 12/2001 | Ohishi | G01C 21/36 |
| | | | 701/425 |
| 2006/0167696 A1 | 7/2006 | Chaar et al. | |
| 2008/0103781 A1* | 5/2008 | Wasson | G10L 17/26 |
| | | | 704/277 |
| 2008/0269958 A1 | 10/2008 | Filev et al. | |
| 2012/0252483 A1* | 10/2012 | Farmer | H04W 4/024 |
| | | | 455/456.1 |
| 2013/0041665 A1* | 2/2013 | Jang | H04N 21/478 |
| | | | 704/246 |
| 2013/0322665 A1* | 12/2013 | Bennett | G01C 21/3638 |
| | | | 381/300 |
| 2014/0278072 A1* | 9/2014 | Fino | G01C 21/362 |
| | | | 701/465 |
| 2014/0372020 A1* | 12/2014 | Stein | G01C 21/3644 |
| | | | 701/410 |
| 2015/0053066 A1* | 2/2015 | Hampiholi | G10H 1/0008 |
| | | | 84/602 |
| 2016/0033280 A1* | 2/2016 | Moore | G06K 9/00671 |
| | | | 701/472 |
| 2016/0036962 A1* | 2/2016 | Rand | H04M 1/72563 |
| | | | 455/418 |
| 2016/0265917 A1* | 9/2016 | Yamamoto | A61H 3/06 |
| 2017/0011210 A1* | 1/2017 | Cheong | G06F 21/32 |
| 2017/0174230 A1* | 6/2017 | Goldman-Shenhar | B60W 50/10 |
| 2018/0005625 A1* | 1/2018 | Han | G06N 20/00 |
| 2019/0355351 A1* | 11/2019 | Kim | B60W 50/087 |

OTHER PUBLICATIONS

Mittal R., "In-Vehicle Multimodal Interaction an Approach to Mitigate Driver Distraction", Arizona State University, 2015, 120 pages.

* cited by examiner

USER EXPERIENCE EVALUATION

I. FIELD

The present disclosure is generally related to systems that identify and perform tasks responsive to receiving user inputs, and more particularly to evaluating a user experience with such systems.

II. DESCRIPTION OF RELATED ART

Some audio-based systems, such as vehicle navigation systems or smart speaker systems, are capable of receiving spoken commands from a user and performing an action based on the command. For example, the user may speak the command "play music on the living room speaker." A smart speaker may perform natural language processing (NLP) on the user speech (or a text string based on the user speech) to identify the action to be performed. However, if the action to be performed is incorrectly identified, the user may become frustrated, thus degrading the user's experience. Repeating the command may lead to repeated misidentification of the command in the user's speech, such as when ambient noise is interfering with the system's ability to recognize the user's speech, further increasing the user's frustration. Although in some cases the system may correctly identify the user's repeated command, in other cases the user may choose to discontinue using the system rather than having to repeat the command once again. In either situation, the user's interaction with the system results in a negative user experience and a reduced likelihood that the user will use the system again.

III. SUMMARY

In a particular aspect, a device includes a memory configured to store a user experience evaluation unit and a processor coupled to the memory. The processor is configured to receive a first user input corresponding to a user command to initiate a particular task. The first user input is received via a first sensor. The processor is configured to, after receiving the first user input, receive one or more subsequent user inputs. The one or more subsequent user inputs include a second user input received via a second sensor. The processor is also configured to initiate a remedial action in response to determining, based on the user experience evaluation unit, that the one or more subsequent user inputs correspond to a negative user experience.

In another particular aspect, a method for operating a device based on a determined user experience includes receiving, at a processor, a first user input corresponding to a user command to initiate a particular task. The first user input is received via a first sensor. The method includes, after receiving the first user input, receiving one or more subsequent user inputs. The one or more subsequent user inputs include a second user input received via a second sensor. The method also includes initiating a remedial action in response to determining, based on a user experience evaluation unit, that the one or more subsequent user inputs correspond to a negative user experience.

In another particular aspect, an apparatus includes means for receiving a first user input corresponding to a user command to initiate a particular task. The first user input is received via a first sensor. The apparatus includes means for receiving one or more subsequent user inputs. The one or more subsequent user inputs include a second user input received via a second sensor after the first user input is received. The apparatus also includes means for initiating a remedial action in response to determining, based on a user experience evaluation unit, that the one or more subsequent user inputs correspond to a negative user experience.

In another particular aspect, a non-transitory computer readable medium stores instructions that, when executed by a processor, cause the processor to initiate, perform, or control operations including receiving a first user input corresponding to a user command to initiate a particular task. The first user input is received via a first sensor. The operations include, after receiving the first user input, receiving one or more subsequent user inputs, the one or more subsequent user inputs include a second user input received via a second sensor. The operations include initiating a remedial action in response to determining, based on a user experience evaluation unit, that the one or more subsequent user inputs correspond to a negative user experience.

Other aspects, advantages, and features of the present disclosure will become apparent after review of the entire application, including the following sections: Brief Description of the Drawings, Detailed Description, and the Claims.

IV. BRIEF DESCRIPTION OF THE DRAWINGS

V. DETAILED DESCRIPTION

Figure 1:
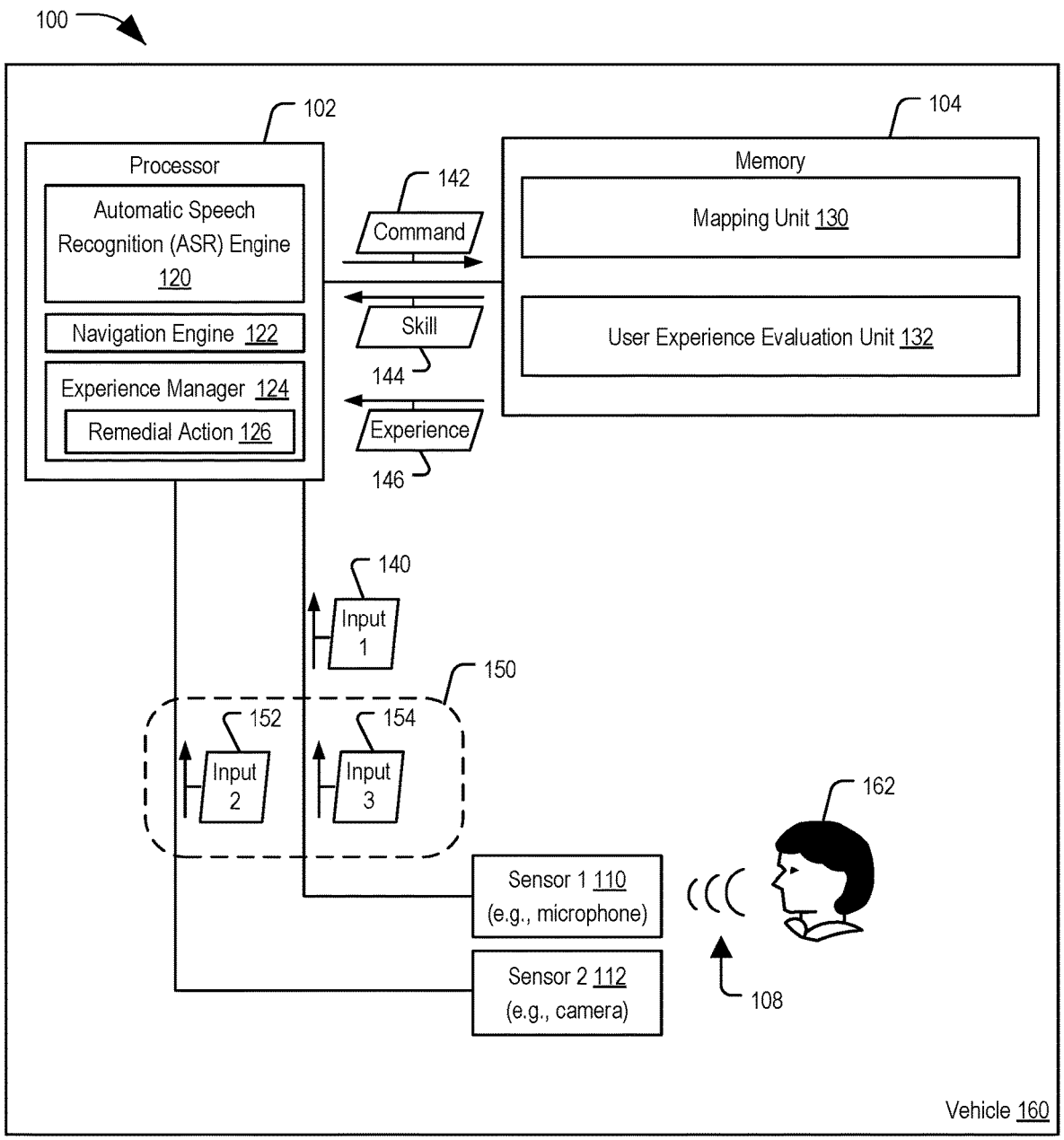
FIG. 1 is a block diagram of a particular illustrative aspect of a system that performs user experience evaluation.

Particular aspects of the present disclosure are described below with reference to the drawings. In the description, common features are designated by common reference numbers throughout the drawings. As used herein, various terminology is used for the purpose of describing particular implementations only and is not intended to be limiting. For example, the singular forms "a," "an," and "the" are intended to include the plural forms as well, unless the context clearly indicates otherwise. It may be further understood that the terms "comprise," "comprises," and "comprising" may be used interchangeably with "include," "includes," or "including." Additionally, it will be understood that the term "wherein" may be used interchangeably with "where." As used herein, "exemplary" may indicate an example, an implementation, and/or an aspect, and should not be construed as limiting or as indicating a preference or a preferred implementation. As used herein, an ordinal term (e.g., "first," "second," "third," etc.) used to modify an element, such as a structure, a component, an operation, etc., does not by itself indicate any priority or order of the element with respect to another element, but rather merely distinguishes the element from another element having a same name (but for use of the ordinal term). As used herein, the term "set" refers to a grouping of one or more elements, and the term "plurality" refers to multiple elements.

In the present disclosure, terms such as "determining", "calculating", "estimating", "shifting", "adjusting", etc. may be used to describe how one or more operations are performed. It should be noted that such terms are not to be construed as limiting and other techniques may be utilized to perform similar operations. Additionally, as referred to herein, "generating", "calculating", "estimating", "using", "selecting", "accessing", and "determining" may be used interchangeably. For example, "generating", "calculating", "estimating", or "determining" a parameter (or a signal) may refer to actively generating, estimating, calculating, or determining the parameter (or the signal) or may refer to using, selecting, or accessing the parameter (or signal) that is already generated, such as by another component or device.

As used herein, "coupled" may include "communicatively coupled," "electrically coupled," or "physically coupled," and may also (or alternatively) include any combinations thereof. Two devices (or components) may be coupled (e.g., communicatively coupled, electrically coupled, or physically coupled) directly or indirectly via one or more other devices, components, wires, buses, networks (e.g., a wired network, a wireless network, or a combination thereof), etc. Two devices (or components) that are electrically coupled may be included in the same device or in different devices and may be connected via electronics, one or more connectors, or inductive coupling, as illustrative, non-limiting examples. In some implementations, two devices (or components) that are communicatively coupled, such as in electrical communication, may send and receive electrical signals (digital signals or analog signals) directly or indirectly, such as via one or more wires, buses, networks, etc. As used herein, "directly coupled" may include two devices that are coupled (e.g., communicatively coupled, electrically coupled, or physically coupled) without intervening components.

Systems and methods enable evaluation of a user experience and initiation of one or more remedial actions if the user experience is determined to be negative or otherwise unsatisfactory. Misinterpretation of a user command, such as a command uttered by a user and interpreted via a speech interface of the system, may be detected based on multi-modal analytics in some implementations. For example, user experience evaluation may include speech keyword detection, such as detection of power expressions, meaningless words, or exclamations (e.g., curse words). User experience evaluation may include audio emotion analysis, video emotion analysis, or both, such as to detect a user's frustration level or happiness level. User experience evaluation may include prosody analytics determined based on the user's voice feedback and audio event detection to detect events such as laughter, arguments, or a baby crying, as non-limiting examples. If a user's experience is detected as being negative, one or more remedial actions may be selected to help calm the user, to help circumvent the source of the negative experience, to update the system to prevent or reduce the likelihood of future negative experiences, or a combination thereof.

FIG. 1 depicts an illustrative example of a system 100 that includes a processor 102 coupled to a memory 104, a first sensor 110, and a second sensor 112. The system 100 is configured to interpret a command based on user input and to initiate performance of a task based on the command. The system 100 is also configured to evaluate a user experience after initiating performance of the task and to select a remedial action to be performed if the user is determined to have a negative experience. The remedial action is selected to improve the user's experience, such as by helping calm the user, by helping circumvent the source of the negative experience, by performing an update to prevent or reduce the likelihood of future negative experiences, or a combination thereof.

The processor 102, the memory 104, and the sensors 110, 112 are implemented in a vehicle 160, such as a car. (In other implementations, the processor 102, the memory 104, and the sensors 110, 112 are implemented in other devices or systems, such as a smart speaker system or a mobile device, as described further below). The first sensor 110 and the second sensor 112 are each configured to capture user input received from a user 162, such as an operator of the vehicle 160. For example, the first sensor 110 may include a microphone configured to capture user speech 108, and the second sensor 112 may include a camera configured to capture images or video of the user 162. The first sensor 110 and the second sensor 112 are configured to provide user input to the processor 102. For example, the first sensor 110 is configured to capture and provide to the processor 102 a first user input 140 (e.g., first audio data) indicating a user's command. The user speech 108 may be an utterance from the user 162, such as a driver or passenger of the vehicle 160. In a particular implementation, the first user input 140 corresponds to keyword-independent speech (e.g., speech that does not include a keyword as the first word). The second sensor 112 is configured to provide a second user input 152 (e.g., a video input including non-verbal user information) to the processor 102.

The memory 104 includes a mapping unit 130 and a user experience evaluation unit 132. The mapping unit 130 is executable by the processor 102 to map received commands, such as a command 142, into operations (also referred to as "tasks" or "skills") to be performed responsive to the command 142. Examples of skills that may be supported by the system 100 include "navigate to home," "turn on radio," "call Mom," or "find a gas station near me." The mapping unit 130 is executable to return a particular skill 144 that corresponds to a received command 142. The user experience evaluation unit 132 is configured to determine, based on one or more received inputs, experience data 146 indicating aspects of an experience of the user 162. For example, the user experience evaluation unit 132 may evaluate a user experience based on at least one of speech keyword detection, audio emotion analytics, video emotion analytics, prosody analytics, or audio event detection. In some implementations, the mapping unit 130, the user experience evaluation unit 132, or both, is dynamically adjustable and updated based on user feedback. Implementations of the mapping unit 130 and the user experience evaluation unit 132 are described in further detail with reference to FIGS. 2-4.

The processor 102 includes an automatic speech recognition (ASR) engine 120, a navigation engine 122, and an experience manager 124. The ASR engine 120 is configured to receive audio input corresponding to user speech and to generate an output indicating detected speech in the audio input. For example, in some implementations, the ASR engine 120 generates a textual output that identifies words detected in an audio input. To illustrate, the ASR engine 120 may process an audio portion of the first user input 140 and generate a textual output that includes a detected command 142 spoken by the user 162. In some implementations, the processor 102 is configured to determine whether input data includes speech prior to attempting to convert the input data to a textual output. For example, the processor 102 may perform voice activity detection (VAD) on the input data, and if a voice activity level satisfies a threshold, the input data (or a portion thereof) may be identified as speech. If the voice activity level does not satisfy the threshold, the input data may be discarded (or otherwise not further processed).

The navigation engine 122 is configured to perform one or more operations associated with the vehicle 160. For example, the navigation engine 122 may be configured to determine a position of the vehicle 160 relative to one or more electronic maps, plot a route from a current location to a user-selected location, or navigate the vehicle 160 (e.g., in an autonomous mode of vehicle operation), as illustrative, non-limiting examples.

The experience manager 124 is configured to receive the experience data 146 from the user experience evaluation unit 132. The experience data 146 may include a classifier of the user experience as "good" or "bad" (e.g., data having a value between 0 and 1, with a "1" value indicating the user experience is positive and a "0" value indicating the user experience is negative). In other examples the experience data 146 may include multiple values, such as a first value indicating a measurement of happiness, a second value indicating a measurement of anger, a third value indicating a measurement of frustration, a fourth value indicating a measurement of sadness, and a fifth value indicating a measurement of excitement, as illustrative, non-limiting examples.

The experience manager 124 is configured to determine whether the experience data 146 indicates a negative user experience. In a particular example, the experience manager 124 is configured to determine a negative user experience in response to one or more values of the experience data 146 (e.g., a good/bad classifier) being lower than a threshold value (e.g., 0.5). As another example, the experience manager 124 may be configured to generate a weighted sum of multiple values of the experience data 146 (e.g., by adding values for happiness and excitement and subtracting values for anger, frustration, and sadness) and may compare the weighted sum to a threshold value to determine whether the experience data 146 corresponds to a negative user experience.

In response to determining that the experience data 146 indicates a negative user experience, the experience manager 124 is configured to initiate performance of a remedial action 126. In a first example, the remedial action 126 includes prompting the user for a non-audio input indicating a user-selected task to be associated with the user command. To illustrate, when the negative user experience results from an incorrect skill 144 being selected for the command 142, the remedial action 126 may be selected to correct the mis-identification of the skill 144 and may include prompting the user 162 to indicate the task that should be associated with the command 142. If the command 142 is determined based on audio input, the user 162 may be prompted, via a visual or audible prompt, for a non-audio input (e.g., to select a task via a touchscreen or via a gesture) to indicate the user-selected task to be associated with the user command 142. Entry of the non-audio input, such as via a touchscreen display device or a gesture detected via a camera, may reduce further user frustration in circumstances where high ambient noise degrades performance of the ASR engine 120 and causes inaccurate interpretation of the user's speech 108.

In another example, the remedial action 126 includes suggesting that the user 162 perform one or more actions to enhance speech recognition of audio captured by a microphone. To illustrate, when high ambient noise degrades performance of the ASR engine 120 and causes inaccurate interpretation of the user's speech 108, the remedial action 126 may include instructing the user 162 to close an open window, to direct the speech 108 toward a microphone (e.g., to speak toward the first sensor 110), to speak more loudly or distinctly, or a combination thereof.

In another example, the remedial action 126 is selected to reduce a negative aspect of the user experience by improving a mood of the user 162. To illustrate, the remedial action 126 may include one or more of playing soothing music, adjusting a voice interface to speak to the user 162 in a calming manner or to have a calming effect, or recommending a relaxing activity for the user 162. User-specific data may be accessible to the processor 102 to provide selectable options for calming the user 162, such as may have been identified by the user 162 during generation of a user profile for the user 162. For example, the user 162 may input to the system 100 the user's preferences for relaxation, such as particular music or ambient sounds (e.g., a waterfall) and a preferred volume, a particular temperature setting, or a suspension or performance setting of the vehicle 160, as illustrative, non-limiting examples.

Alternatively, or in addition, one or more options for calming the user 162 may be automatically determined by recognizing (e.g., based on a correlation value of historical experience scores and associated actions and circumstances corresponding to the historical experience scores) which actions and circumstances are highly correlated with a positive user experience, a positive change in the user experience, or a combination thereof. As an example, the processor 102 may determine, during analysis of a history of interactions with the user 162, a high correlation between travelling to a house of a sister of the user 162 and a detected transition from a negative user experience to a positive user experience. As a result, the experience manager 124 may generate an output to be presented to the user 162, such as "Would you like to visit your sister today?" as the remedial action 126. In this manner, the processor 102 may be configured to monitor the user's emotional state and to correlate the emotional state (or changes to the emotional state) to one or more operations for later use in improving the user's mood in response to detecting a negative experience.

An example of operation is described below in an implementation in which the first sensor 110 is a microphone and the second sensor 112 is a camera. The user 162 speaks a command such as "go home," indicating that the user 162 wants the navigation engine 122 to plot a route to the user's home on a map displayed on a vehicle navigation screen. The first sensor 110 generates a first user input 140 that corresponds to the user command (e.g., "go home") to initiate a particular task (e.g., plot the route).

The ASR engine 120 processes audio data of the first user input 140 and generates the command 142. Due to an amount of wind noise in the vehicle 160, the ASR engine 120 may unsuccessfully interpret the command 142 as "go Rome". As a result, the processor 102 accesses the mapping unit 130 using the user command 142, the mapping unit 130 maps the command 142 to a personal assistant task to initiate travel plans to Rome, Italy, and outputs the skill 144. The processor 102 initiates the skill 144, selected by the mapping unit 130, by prompting the user 162 via a voice interface, "Ok. Let's plan a trip to Rome. On what day would you like to depart?"

After receiving the first user input 140 and initiating performance of the skill 144 to plan a trip to Rome, the processor 102 receives one or more subsequent user inputs 150 including a second user input 152 received via the second sensor 112 and a third user input 154 (e.g., an audio input including one or more utterances of the user 162)

received via the first sensor 110. The user experience evaluation unit 132 processes the second user input 152 and the third user input 154 to determine the experience data 146.

For example, as described in further detail with reference to FIG. 4, the user experience evaluation unit 132 may evaluate video data of the second user input 152 to detect gestures indicating a negative user experience, such as fist-shaking, teeth-clenching, or a tense posture, or gestures indicating a positive user experience, such as smiling, whistling, or a relaxed posture. The user experience evaluation unit 132 may evaluate audio data of the third user input 154 to detect keywords, vocal intonations, or other characteristics of the user's speech 108 that may be indicative of a positive user experience or a negative user experience.

If the experience data 146 indicates a positive user experience, the experience manager 124 may determine that the skill 144 was correctly selected and no remedial action is to be performed. Otherwise, in response to the experience data 146 indicating that the user inputs 152, 154 correspond to a negative user experience, the experience manager 124 may select and initiate performance of a remedial action 126. For example, the experience manager 124 may prompt the user 162 for feedback to determine whether the skill 144 was misidentified, may provide suggestions to the user 162 to reduce errors in identifying the command 142 (e.g., removing sources of ambient noise), or may initiate actions to calm or soothe the user 162, such as playing relaxing music. In some implementations the system 100 prompts the user 162 to confirm whether the command 142, the skill 144, or both, is correct and if not correct, the system 100 prompts the user 162 to repeat the command.

In some implementations, such as when the user 162 is operating the vehicle 160, the experience manager 124 may delay performance of the remedial action 126 until the user 162 has shut off the vehicle 160, the user 162 is detected to have a non-negative user experience, or both. For example, the remedial action 126 may be delayed until the negative user experience is detected to have ended. Thus, the experience manager 124 may avoid requesting user feedback or otherwise engaging in non-essential interaction with the user 162 while the user 162 is experiencing negative emotions and operating the vehicle 160. As a result, a possibility of worsening the user's experience may be decreased, and user safety in operating the vehicle 160 may be increased.

By detecting that the user 162 has a negative user experience and initiating the remedial action 126, the system 100 may improve an overall experience of the user 162. For example, when the remedial action 126 includes identifying and correcting a misidentified command, the user's experience may be improved. In another example the remedial action 126 is operative to soothe or calm the user 162, and the user's experience may be immediately enhanced as compared to the user's experience prior to performing the remedial action 126. As another example, when the remedial action 126 includes receiving user feedback regarding the source of dissatisfaction (e.g., misidentification of the command 142), use of the feedback to update and adapt the mapping unit 130 results in reduced future mispredictions of the command 142 (via operation of the updated mapping unit 130) and an enhancement of future experiences of the user 162.

Although the first sensor 110 and the second sensor 112 are described with reference to a microphone and a camera, respectively, in other implementations the first sensor 110 and the second sensor 112 correspond to other types of sensors. For example, the first sensor 110 may correspond to a camera, a biometric sensor, or another type of sensor, and the second sensor 112 may correspond to a microphone, a biometric sensor, or another type of sensor. Although two sensors are shown, in other implementations more than two sensors are included, such as described with reference to FIG. 2.

Although the system 100 is depicted in a vehicle 160, such as a car, a boat, a plane, etc., in other implementations the system 100 is not implemented in a vehicle and may instead be implemented as part of a smart speaker device, as part of a home or building automation system, or a combination thereof. To illustrate, in a particular implementation, the system 100 is implemented in a smart speaker system (e.g. a wireless speaker and voice command device that is integrated with a virtual assistant, responsive to user commands such as "what movies are out now?" or "call Mom"). In another particular implementation, the system 100 is implemented in a mobile device, such as a mobile phone, a laptop computer, a tablet computer, a computerized watch, etc. In another particular implementation, the system 100 is implemented in one or more Internet of Things (IoT) devices or smart appliances, as non-limiting examples.

Figure 2:
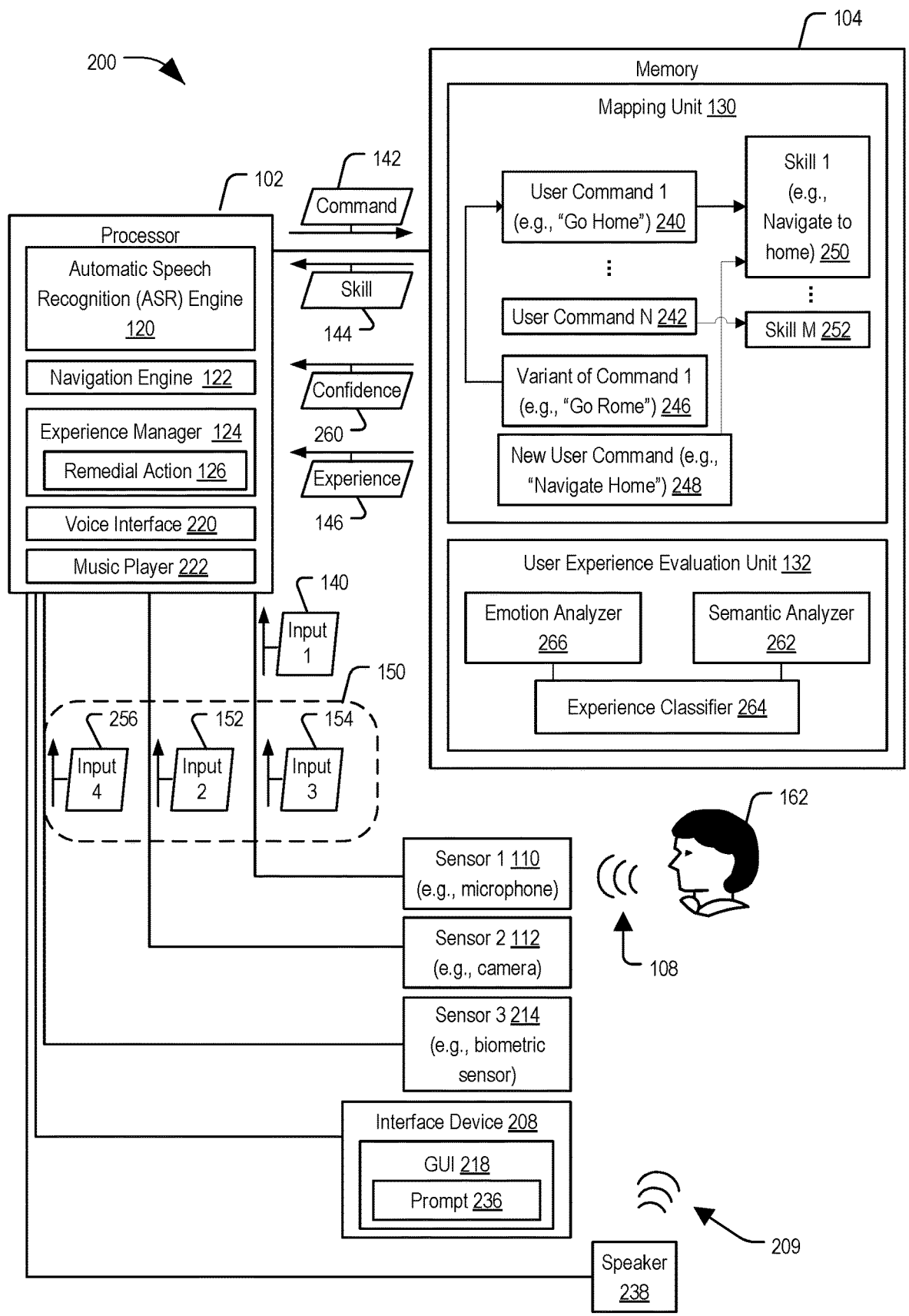
FIG. 2 is a block diagram of a particular illustrative aspect of a system to perform user experience evaluation.

Referring to FIG. 2, an illustrative implementation of a system configured to perform user experience evaluation is shown and generally designated 200. In a particular implementation, the system 200 may include or correspond to the system 100. Each of the elements of the system 200 may be represented in hardware, such as via an application-specific integrated circuit (ASIC) or a field-programmable gate array (FPGA), or the operations described with reference to the elements may be performed by a processor executing computer-readable instructions.

The system 200 includes the processor 102, the memory 104, the first sensor 110, and the second sensor 112 of FIG. 1. The system 200 also includes a third sensor 214, an interface device 208, and a speaker 238. In a particular example, the third sensor 214 includes one or more biometric sensors that provide data, such as heart rate, body temperature, other measurements, or a combination thereof, that may be used to help determine an emotional state of the user. The interface device 208 may include a display to provide visual information to the user 162 and a touchscreen, keypad, or other input device to receive input from the user 162. The speaker 238 may be configured to output audible information to the user 162, such as speech 209.

The processor 102 accesses the mapping unit (e.g., a model) 130 in the memory 104 to determine whether the user command 142 is mapped to a task. As illustrated, the mapping unit 130 includes multiple stored commands 240-242 that are mapped to multiple skills 250-252 (mappings are indicated by arrows). The mapping unit 130 may be included in a natural language processing (NLP) system and configured to generate a confidence score associated with a particular task in response to receiving the user command 142. For example, the mapping unit 130 may include a convolutional neural network that generates a confidence score for each of the user commands 240-242, with the highest confidence score indicating a best determined match between the user command 142 and the stored commands 240-242 (e.g., a "softmax" score after a final fully connected layer of the convolutional neural network). A particular skill 144 that is mapped to the best user command match is provided to the processor 102 and may be associated with a confidence score 260.

After the processor 102 initiates execution of the skill 144, subsequent user inputs 150 are provided to the processor 102 from various sensors and are processed by the user experience evaluation unit 132 for information regarding the user's experience. For example, the subsequent user inputs 150 include the second user input 152 including video content of the user 162, the third user input 154 including one or more utterances of the user 162, and a fourth input 256 from the third sensor 214, such as a heart rate measurement of the user 162.

The user experience evaluation unit 132 includes an emotion analyzer 266 configured to determine a satisfaction or frustration level of the user 162 based on emotion cues detected in the subsequent user inputs 150. The emotion analyzer 266 includes an audio emotion analyzer, a video emotion analyzer, or a combination thereof. The user experience evaluation unit 132 also includes a semantic analyzer 262 configured to determine an emotional state of the user 162 based on semantic cues detected the subsequent user inputs 150. Outputs of the emotion analyzer 266 and the semantic analyzer 262 are processed at an experience classifier 264 that is configured to output the experience data 146. Further details of components and operation of the user experience evaluation unit 132 are described with reference to the example of FIG. 4.

The experience manager 124 processes the experience data 146 to determine whether a remedial action should be performed and to select a particular remedial action 126. For example, if the experience data 146 indicates a non-negative user experience (e.g., a neutral or positive user experience), the experience manager 124 may determine that no remedial action is to be performed. Otherwise, the experience manager 124 selects one or more remedial actions to perform.

For example, in an implementation where the system 200 provides information to the user 162 via speech, the experience manager 124 may send a control signal to a voice interface 220. The control signal may case the voice interface 220 to adjust operation to provide a more calming or soothing manner of speech with the user 162. The voice interface 220 may adjust a tone, rate of speech, vocabulary, one or more other factors, or a combination thereof, to present speech 209 having qualities designed to improve an emotional state of the user 162.

As another example, the experience manager 124 may adjust operation of a music player 222, such as an in-vehicle entertainment system. The experience manager 124 may send a control signal to the music player 222 to initiate playing soothing music if no music is currently being played. If the music player 222 is already playing music selected by the user 162, the control signal may cause the volume to be increased (if the music is categorized as calming music, such as an easy-listening radio station) or decreased (if the music is categorized as agitating music, such as a rock-and-roll radio station). In some implementations, the remedial action 126 includes suggesting to the user 162 a change of musical selection, such as based on user preferences or a history of user emotional responses to various types of music. In other implementations, the remedial action 126 includes changing the musical selection without notifying the user 162.

In some circumstances, the remedial action 126 includes updating the mapping unit 130 to reduce future misinterpretations of the user's commands. To illustrate, the system 200 may have incorrectly interpreted the user's command, such as due to a noisy environment or a variation in the user's speech pattern. When the particular skill 144 is not what the user 162 requested, the processor 102 is configured to receive an audio or non-audio input indicating a user-selected task to be associated with the user command 142. A non-audio input, such as an input via a graphical user interface (GUI), a gesture captured by a camera, a touch detected by a touch sensor, or one or more other non-speech input modalities that are generically represented by the interface device 208, may be more reliably interpreted than the user's speech. To illustrate, the interface device 208 may include any type of display device, such as a liquid crystal display (LCD) screen, a touch screen, or a separate monitor or other display, as non-limiting examples and may include any type of input device, such as a keypad, a pointing and selecting device, graphical or physical controls, or any combination thereof, as illustrative, non-limiting examples.

In a particular implementation, the system 200 includes the interface device 208, and a graphical user interface (GUI) 218 is displayed. The GUI 218 enables the user to select a particular skill, such as a "Go Home" navigation operation. The GUI 218 may also play back audio of the first user input 140 and generate a prompt 236 to ask the user 162 for an indication, via an input device (e.g., a touchscreen, a keypad, the first sensor 110, the second sensor 112, etc.), of which skill was requested. The user 162 may input a skill (e.g., via a touchscreen or keypad), or may input the skill using another modality, such as a gesture. In an alternate implementation, the system 200 does not include the interface device 208, and the GUI 218 (including the prompt 236) is displayed on a mobile communication device of the user (e.g., by running an application associated with the system 200). In another implementation, the prompt 236 is provided to the user via an audio prompt, and the user interacts with the system using audio prompts and a touchscreen or keypad, a gesture, or another modality of interactions.

In a particular implementation, the system 200 may determine whether to prompt the user for feedback based on the user experience data 146 and the confidence score 260. For example, after selecting and initiating execution of the particular skill 144, the processor 102 may track one or more indications of the user's reaction via the user experience evaluation unit 132. For example, the experience data 146 is determined based on one or more of speech keyword detection (e.g., the user says "no" or "not again"), audio-video (A/V) emotion analytics, prosody analytics, or audio event detection. A user experience that is detected as negative may be represented as a lower value in the experience data 146 that indicates a lower likelihood that the particular skill 144 is correct, and a user experience that is detected as positive may be represented as a higher value in the experience data 146 that indicates a greater likelihood that the particular skill 144 is correct. When the confidence score 260 is high, the value in the experience data 146 is high, or both, the system 200 may determine that the particular skill 144 is correctly determined and not prompt the user to input the intended skill. However, when both of the confidence score 260 and the experience data 146 have low values, the system 200 may determine that the particular skill 144 is incorrect and may provide the prompt 236 for the user's feedback via the interface device 106.

In response to receiving the non-audio input prompted by the GUI 218, the processor 102 is configured to process the user command. To illustrate, when the user command corresponds to a car-related command (e.g., "go home"), the processor 102 may process the user command by performing the user-selected skill to control the car (e.g., a navigation task to route the car to a "home" location).

The processor 102 is also configured to update the mapping unit 130 to associate the user command 142 with the user-selected skill. After updating the mapping unit 130, the system 200 is more likely to correctly identify the correct user-selected skill when the user next enters the user command 142 and is less likely to select another (incorrect) skill in response to the user command 142. Updating the mapping unit 130 may include at least one of storing the user command 142 as a recognized variant of an existing user command or storing the user command 142 as a new command that is mapped to the user-selected task. For example, if the command 142 is interpreted as "go Rome" and is a mis-identification of the existing user command ("go home") 240, the command 142 may be stored as a recognized variant 246 of the "go home" user command 240 so that future detections of "go Rome" are mapped to the "go home" user command 240. As another example, if the user command 142 is a new user command "navigate home" that the user indicates corresponds to the "navigate to home" skill 250, a new user command ("navigate home") 248 may be added to the mapping unit 130 and mapped to the "navigate to home" skill 250. The mapping unit 130 may be re-trained based on the updated set of user commands, resulting in improved user experience due to reduced misinterpretation of user commands.

By updating the mapping unit 130 based on the user feedback, the system 200 may adaptively respond to errors, reducing misinterpretations in subsequent operation. Because the mapping unit 130 is updated based on the user feedback, the ASR engine 120 may be implemented as an embedded system (e.g., a dedicated system for performing ASR at reduced cost and power consumption as compared to a general-purpose computer but that is not as easily updated) without impairing the capability of the system 200 to improve operation based on user feedback. In addition, using a non-audio input modality to receive the user feedback provides a more reliable feedback mechanism under certain conditions such as high ambient noise that may interfere with an audio input modality.

Figure 3:
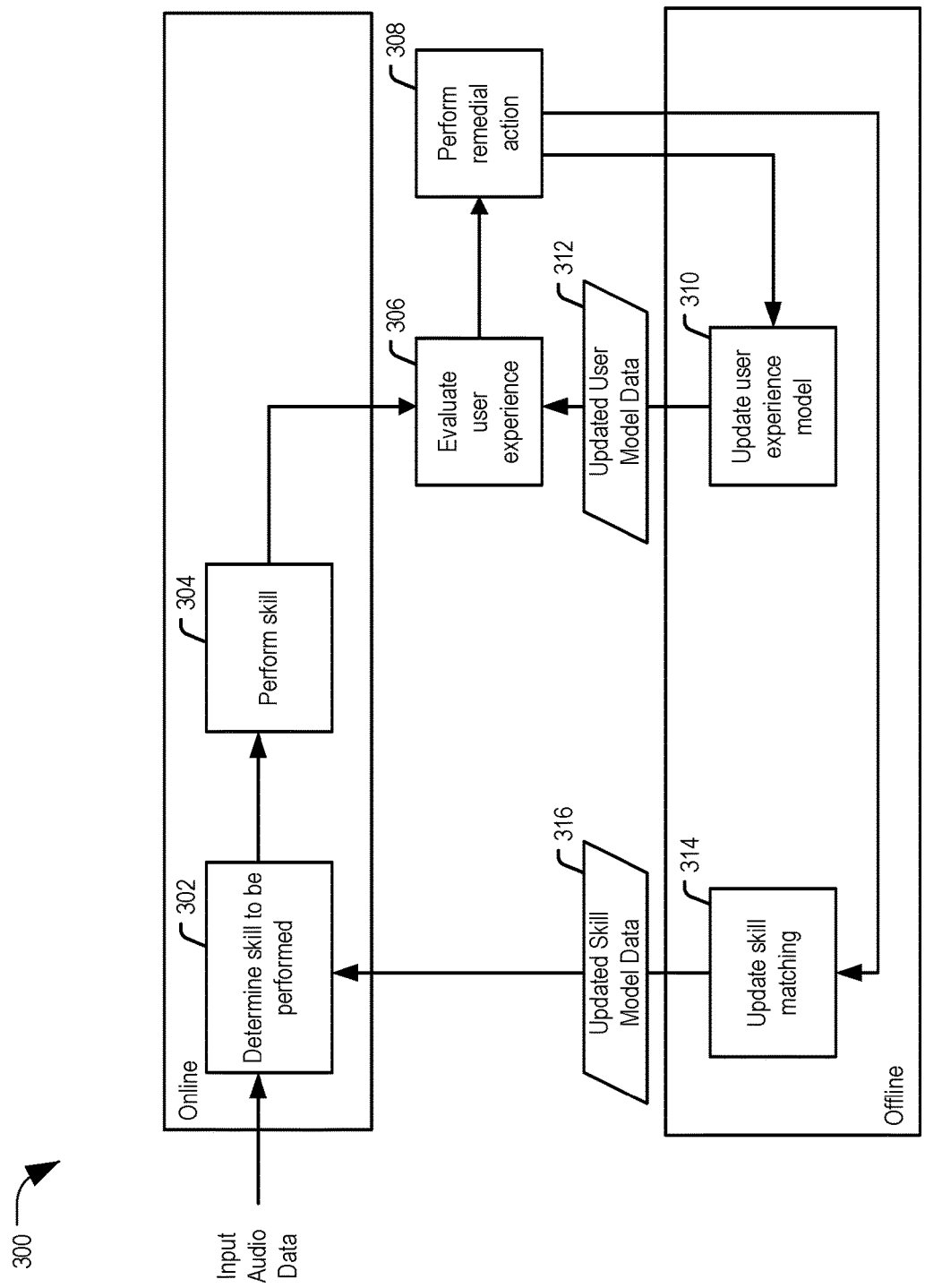
FIG. 3 is a flow chart that illustrates a method of processing user input including evaluating a user experience.

FIG. 3 depicts an example of a method 300 of processing input audio data. The method 300 includes determining a skill to be performed responsive to receiving the input audio data, at 302. For example, determining the skill to be performed may be executed via the automatic speech recognition engine 120 generating the command 142 based on the first user input 140. The command 142 may be used by the mapping unit 130 to select the skill 144, corresponding to the skill to be performed.

The method 300 includes performing the determined skill, at 304. For example, when the skill 144 indicates a navigation skill, the processor 102 may perform the navigation skill via the navigation engine 122. As another example, when the skill 144 corresponds to another skill, such as an in-vehicle entertainment skill, the processor 102 may initiate performance of the skill using a system other than the navigation engine 122, such as the music player 222.

After performing the skill, at 304, a user experience is evaluated, at 306. For example, the processor 102 may receive one or more subsequent user inputs, such as the subsequent user inputs 150 of FIG. 1. The subsequent user inputs may include an audio input, a video input, one or more other inputs such as physiological measurements, or any combination thereof. The subsequent user inputs that are received by the processor 102 after performing the skill may be processed by the user experience evaluation unit 132 to determine one or more aspects of the user experience.

In the event that the user experience is evaluated to be a negative user experience, a remedial action is performed, at 308. To illustrate, the remedial action may correspond to the remedial action 126 that is initiated by the experience manager 124.

In response to performing the remedial action 308, a user experience model may be updated, at 310. For example, when the remedial action 126 includes prompting the user to input a correct skill to be performed, and the user indicates that the system-selected skill was the correct skill, the user experience model may be updated based on updated user model data 312 to indicate that the user's reaction to the skill was not indicative of a mispredicted skill. In an example, the user enters the user command "go home," and the mapping unit 130 correctly interprets the audio command "go home" as a skill that causes the navigation engine 122 to map a route to the user's home. The user is then detected, via the subsequent user inputs, to perform a gesture that is interpreted as indicative of a negative user experience. User feedback that the selected skill was correct may indicate that the detected gesture was not indicative of a mispredicted skill.

To illustrate, the user may have frowned following the display of the navigation route. However, the frown may have resulted from a traffic event occurring near the user's vehicle and may not have been related to performance of the "navigate to home" skill. Thus, updating the user experience model may include generating modified user model data 312 that reduces a weighting factor associated with a frown when evaluating whether a user is negatively reacting to a mis-identified command.

The method 300 also includes updating the skill matching, at 314. For example, in response to receiving feedback from the user indicating that the determined skill was not the skill indicated by the user, one or more entries in the mapping unit 130 may be updated so that the detected command 142 may be more reliably mapped to the requested skill in future interactions. For example, updating the skill matching may include generating updated skill model data 316, such as the variant command entry 246 or the new command entry 248 of FIG. 2, that may be stored for use in conjunction with interpretation of future commands received from the user.

In the particular implementation illustrated in FIG. 3, determining the skill to be performed, at 302, and performing the skill, at 304, may be performed "online," and updating the user experience model, at 310, and updating the skill matching, at 314, may be performed "offline." Online may refer to time periods during which the input audio data is processed, up to performance of the natural language processing. In some implementations, the natural language processing is also performed online. Offline may refer to idle time periods or time periods during which input audio data is not being processed. Because evaluating the user experience, at 306, and performing the remedial action, at 308, may be performed online (e.g., as skills are performed) or offline (e.g., after the user has finished operating a vehicle or after a particular amount of time has expired, such as a day, a week, or a month), evaluating the user experience and performing the remedial action are illustrated as located between the online and the offline sections.

Figure 4:
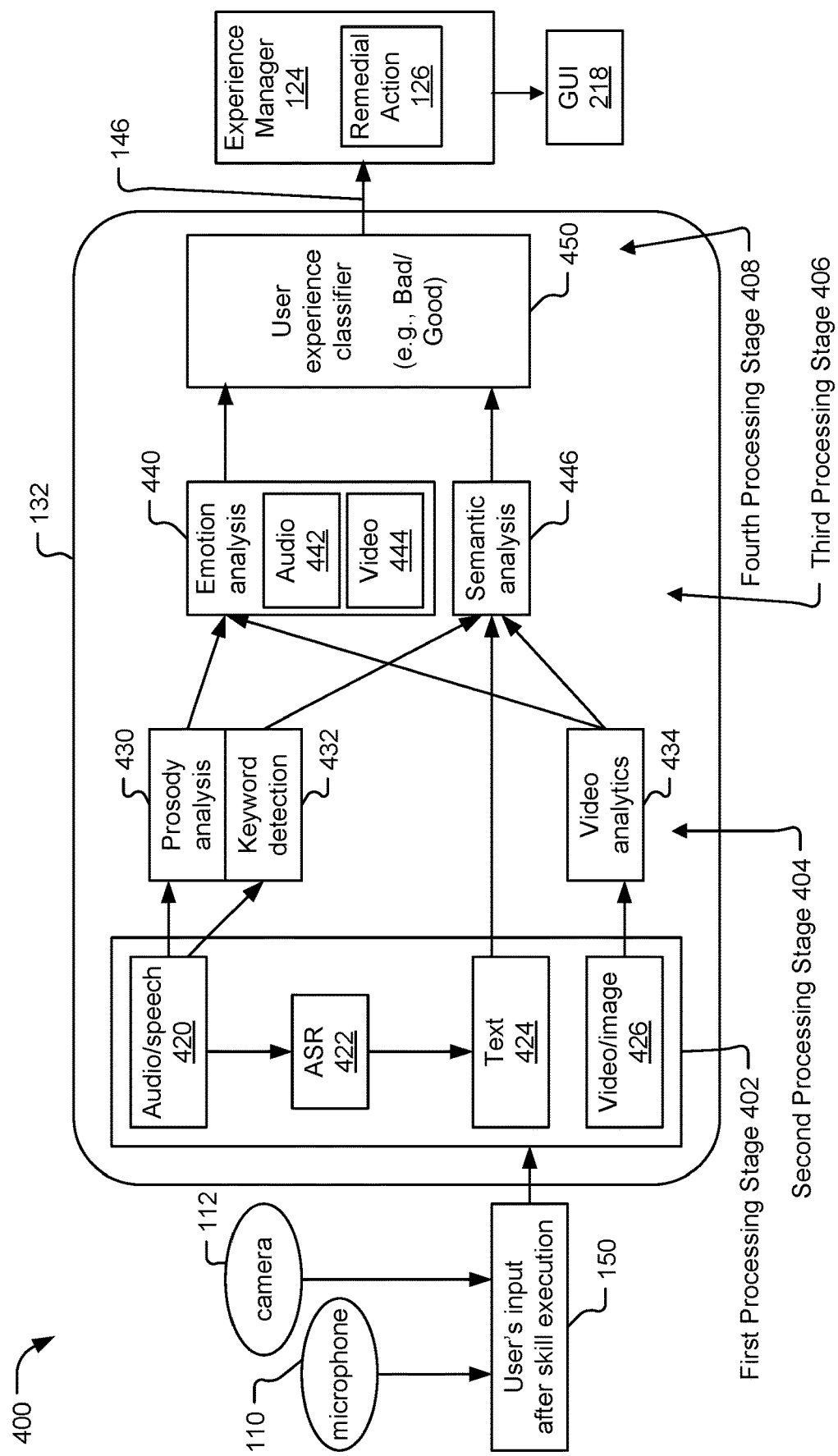
FIG. 4 is a diagram of a particular illustrative aspect of a system to perform user experience evaluation.

FIG. 4 illustrates an example implementation of a system 400 including the first sensor 110 as a microphone, the second sensor 112 as a camera, the user experience evaluation unit 132, the experience manager 124, and the graphical user interface (GUI) 218. The user experience evaluation unit 132 includes a first processing stage 402, a second processing stage 404, a third processing stage 406, and a fourth processing stage 408. For example, the processing stages 402-408 may correspond to layers of a neural network, with each layer corresponding to a different level of analysis of multiple inputs in determining a user experience.

The first processing stage 402 is configured to perform initial processing of user input received after skill initiation, such as the subsequent input 150 of FIG. 1. For example, the first processing stage 402 may perform analysis or preliminary processing of audio and speech data 420, such as by performing an automatic speech recognition operation 422 to generate text 424 detected in the audio and speech data 420. In addition, video and image data 426 may be preliminarily processed by the first processing stage 402.

The second processing stage 404 includes prosody analysis 430, keyword detection 432, and video analytics 434. The prosody analysis 430 is configured to process the audio and speech data 420 to detect one or more prosody elements, such as emphasis, tonality, pitch, speech rate, or one or more other elements that may provide contextual information regarding the detected text 424, such as a particularly long duration. In an illustrative example, duration is one aspect of prosody: if the speech has longer or shorter duration than usual, the user is likely in an emotional state, such as sadness, un-satisfaction, hesitation, etc. Other prosody elements like tonality and pitch contour, with which dynamic range is higher or lower than usual may suggest the user is happy or frustrated with the experience. A relatively complex mapping correlation may exist between all features of prosody and good/bad user experience. The prosody analysis 430 extracts prosody related features as one of the inputs to an emotion analysis 440, as described below.

The keyword detection 432 may be performed to detect occurrences of one or more keywords, such as in a dictionary of exclamations or other utterances associated with user experience. For example, the keyword detection 432 may be configured to detect exclamations such as "no," "not that," "oh no," or any other keyword, power expression, or meaningless word that may indicate a negative user experience. In other implementations, the keyword detection 432 may further be configured to detect exclamations that may be indicative of a positive user experience, such as "excellent," "good," "that's right," "thanks," one or more other exclamations, or any combination thereof.

The video analytics processing 434 is configured to detect one or more physical characteristics of the user 162, such as body language or facial expression. The video analytics processing 434 may include facial expression detection, such as smiling or frowning, or body motion detection, such as nodding, shaking head, or shrugging, or a combination thereof, which may indicate strong emotional feedback.

The third processing stage 406 includes emotion analysis processing 440 and semantic analysis processing 446. The emotion analysis processing 440 includes audio emotion analysis, at 442, and video emotion analysis, at 444. For example, the audio emotion analysis 442 may be configured to receive data corresponding to the prosody analysis 430 and may compare the received data to one or more audio emotional models to determine a likelihood that the user input 150 corresponds to one or more emotional states of the user. Similarly, the video emotion analysis 444 may be configured to compare the results of the video analytics 434 to one or more video emotion analysis models to determine whether the user input 150 corresponds to one or more emotional states of the user. The emotion analysis 440 may generate an output indicating one or more confidence levels that one or more respective emotional states have been detected as being experienced by the user.

The semantic analysis 446 may be responsive to results of the keyword detection 432, the text 424, and the video analytics 434 to determine a satisfaction level associated with the input 150. For example, based on the text inputs from these three modules, for instance, "shaking head" from video analytics 434, "no no no" from keyword detection 432, and "this is not what I meant" from the text 424, the semantic analysis 446 may provide a satisfaction level or positive/negative rating that measures how satisfied the user is with this experience.

The fourth processing stage 408 includes a user experience classifier 450. For example, the user experience classifier 450 may perform a weighted combination of results of the emotion analysis 440 and the semantic analysis 446 to classify an overall user experience as being a net positive (e.g., good) user experience or net negative (e.g., bad) user experience. An output of the user experience classifier 450 may be provided to the experience manager 124 as the experience data 146. The experience manager 124 may selectively determine whether to perform the remedial action 126, such as by displaying a prompt at the GUI 218 to request user input, to correct a mis-identification of the user's spoken command.

In some implementations, a user experience summary is generated (e.g., offline, as in FIG. 3) that includes data such as the detected command 142, the skill executed 144, audio sample clips, video sample clips, or both, at the GUI 218. For example, the user experience summary may be presented to the user as part of a weekly update session. The user may be informed that user frustration was detected, and the user may be prompted to enter feedback regarding the detected user frustration. The user may provide a correction to the command 142 that was transcribed by the ASR 120, a correction to the skill 144 that was intended by the user, or a combination thereof. The user experience model and the skill matching model may be updated based on the user feedback, such as described with reference to FIG. 3.

Figure 5:
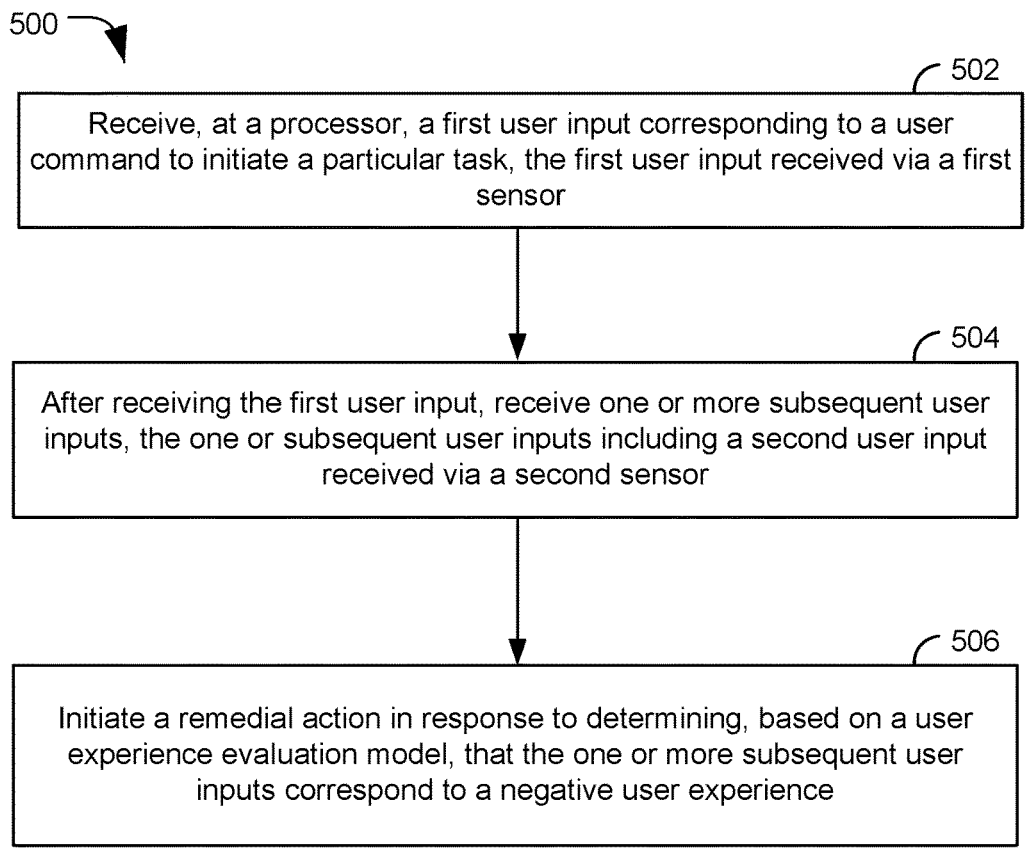
FIG. 5 is a flow chart that illustrates a method of processing user input including evaluating a user experience.

Referring to FIG. 5, a flow chart of an illustrative method of processing user input including evaluating a user experience is shown and generally designated 500. In a particular implementation, the method 500 may be performed by the system 100 of FIG. 1, such as by the processor 102.

The method 500 includes receiving, at a processor, a first user input corresponding to a user command to initiate a particular task, at 502. The first user input is received via a first sensor. For example, the first user input may correspond to the first user input 140 received via the first sensor 110, such as a microphone. In some implementations, the user command is determined based on audio input and the particular task is selected based on the user command.

After receiving the first user input, one or more subsequent user inputs is received, at 504. The one or more subsequent user inputs include a second user input received via a second sensor (e.g., a camera). For example, the one or more subsequent user inputs may correspond to the subsequent user inputs 150 of FIG. 1 including the second user input 152 and the third user input 154 (e.g., audio input) or the subsequent user inputs 150 of FIG. 2 further including the fourth input 256 (e.g., a biometric input).

A remedial action is initiated in response to determining, based on a user experience evaluation unit, that the one or more subsequent user inputs correspond to a negative user experience, at 506. To illustrate, the remedial action may correspond to the remedial action 126 initiated by the experience manager 124. In some implementations, determining that the one or more subsequent user inputs correspond to a negative user experience includes performing at least one of speech keyword detection, audio emotion analytics, video emotion analytics, prosody analytics, or audio event detection, such as described with reference to the user experience evaluation unit 132 of FIG. 2 and FIG. 4.

In an illustrative example, the remedial action includes prompting the user for a non-audio input indicating a user-selected task to be associated with the user command, such as via the GUI 218 of FIG. 2. In an illustrative example, the remedial action includes suggesting that the user perform one or more actions to enhance speech recognition of audio captured by a microphone. In an illustrative example, the remedial action includes playing calming music to improve the user's emotional state.

By detecting that the user has a negative user experience and initiating the remedial action, the method 500 may improve an overall experience of the user. For example, when the remedial action is operative to soothe or calm the user, the user's experience may be immediately enhanced. As another example, when the remedial action includes receiving user feedback regarding the source of dissatisfaction (e.g., misidentification of the command), use of the feedback to update and adapt command recognition results in reduced future mispredictions of the command and an enhancement of future experiences of the user.

Figure 6:
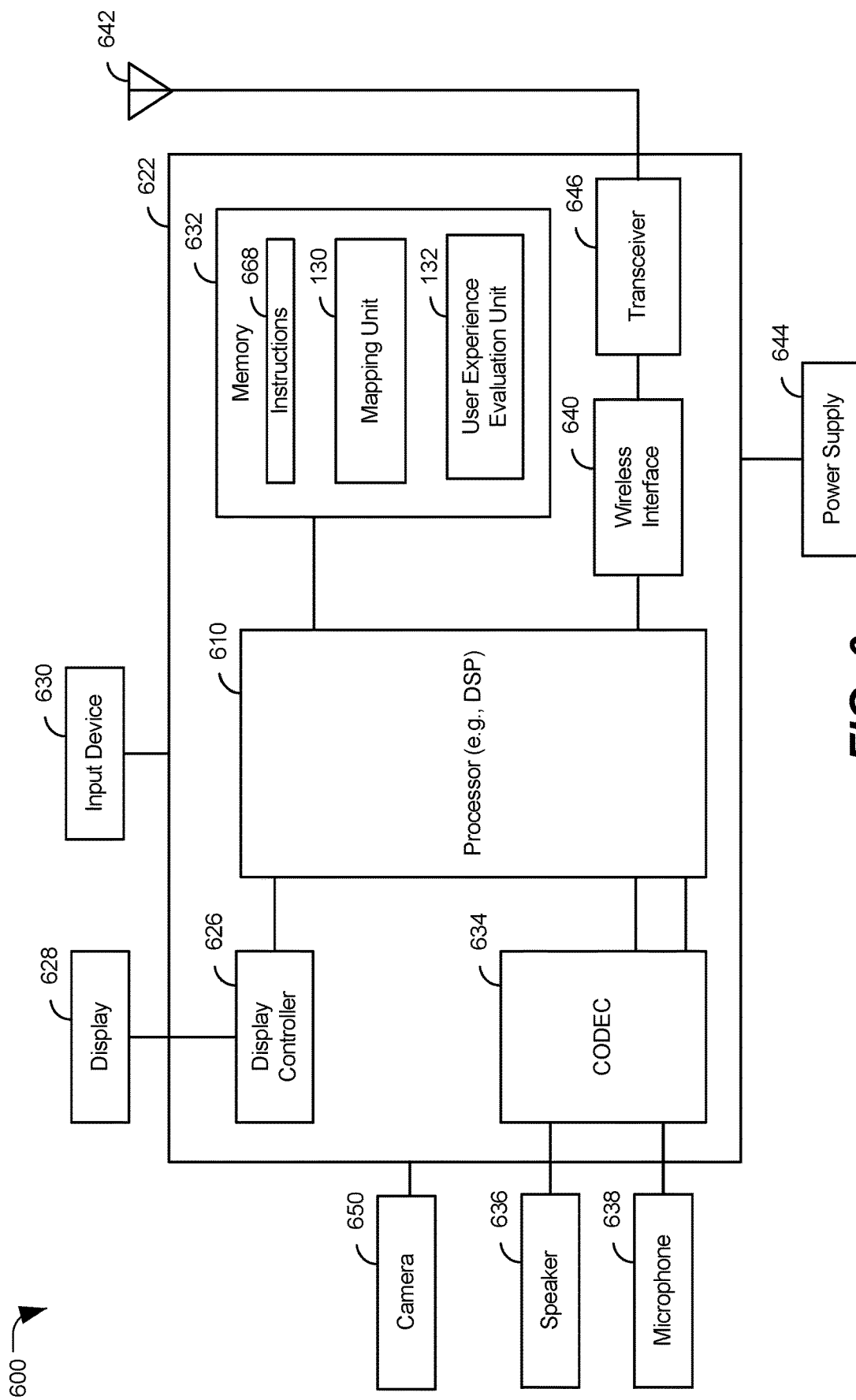
FIG. 6 is a block diagram of an aspect of a wireless device to perform user experience evaluation.

Referring to FIG. 6, a block diagram of a particular illustrative implementation of a device (e.g., a wireless communication device) is depicted and generally designated 600. In various implementations, the device 600 may have more or fewer components than illustrated in FIG. 6. In an illustrative aspect, the device 600 may perform one or more operations described with reference to systems and methods of FIGS. 1-5.

In a particular implementation, the device 600 includes a processor 610, such as a central processing unit (CPU) or a digital signal processor (DSP), coupled to a memory 632. The memory 632 includes instructions 668 (e.g., executable instructions) such as computer-readable instructions or processor-readable instructions. The instructions 668 may include one or more instructions that are executable by a computer, such as the processor 610. The memory 632 also includes the mapping unit 130 and the user experience evaluation unit 132, as described with reference to FIG. 1.

The device 600 may include a display controller 626 that is coupled to the processor 610 and to a display 628. A coder/decoder (CODEC) 634 may also be coupled to the processor 610. A speaker 636 and a microphone 638 may be coupled to the CODEC 634. The device 600 may also include a camera 650.

FIG. 6 also illustrates that a wireless interface 640, such as a wireless controller, and a transceiver 646 may be coupled to the processor 610 and to an antenna 642, such that wireless data received via the antenna 642, the transceiver 646, and the wireless interface 640 may be provided to the processor 610. In some implementations, the processor 610, the display controller 626, the memory 632, the CODEC 634, the wireless interface 640, and the transceiver 646 are included in a system-in-package or system-on-chip device 622. In some implementations, an input device 630 and a power supply 644 are coupled to the system-on-chip device 622. Moreover, in a particular implementation, as illustrated in FIG. 6, the display 628, the input device 630, the speaker 636, the microphone 638, the antenna 642, the power supply 644, and the camera 650 are external to the system-on-chip device 622. In a particular implementation, each of the display 628, the input device 630, the speaker 636, the microphone 638, the antenna 642, the power supply 644, and the camera 650 may be coupled to a component of the system-on-chip device 622, such as an interface or a controller.

In an illustrative implementation, the memory 632 includes or stores the instructions 668 (e.g., executable instructions), such as computer-readable instructions or processor-readable instructions. For example, the memory 632 may include or correspond to a non-transitory, computer readable medium storing the instructions 668. The instructions 668 may include one or more instructions that are executable by a computer, such as the processor 610.

In a particular implementation, the device 600 includes a non-transitory, computer readable medium (e.g., the memory 632) storing instructions (e.g., the instructions 668) that, when executed by a processor (e.g., the processor 610), may cause the processor to initiate, perform, or control operations including receiving a first user input (e.g., the first user input 140) corresponding to a user command to initiate a particular task, the first user input received via a first sensor (e.g., the first sensor 110, the microphone 638). The operations include, after receiving the first user input, receiving one or more subsequent user inputs, the one or more subsequent user inputs including a second user input (e.g., the second user input 152) received via a second sensor (e.g., the second sensor 112, the camera 650). The operations include initiating a remedial action in response to determining, based on a user experience evaluation unit (e.g., the user experience evaluation unit 132), that the one or more subsequent user inputs correspond to a negative user experience.

The device 600 may include a wireless telephone, a mobile communication device, a mobile device, a mobile phone, a smart phone, a cellular phone, a laptop computer, a desktop computer, a computer, a tablet computer, a set top box, a personal digital assistant (PDA), a display device, a television, a gaming console, an augmented reality (AR) device, a virtual reality (VR) device, a music player, a radio, a video player, an entertainment unit, a communication device, a fixed location data unit, a personal media player, a digital video player, a digital video disc (DVD) player, a tuner, a camera, a navigation device, a decoder system, an encoder system, a vehicle, a component of a vehicle, or any combination thereof.

It should be noted that various functions performed by the one or more components of the systems described with reference to FIGS. 1, 2, 4 and the device 600 are described as being performed by certain components or circuitry. This division of components and circuitry is for illustration only. In an alternate aspect, a function performed by a particular component may be divided amongst multiple components. Moreover, in an alternate aspect, two or more components described with reference to FIGS. 1-6 may be integrated into a single component. Each component described with reference to FIGS. 1-6 may be implemented using hardware (e.g., a field-programmable gate array (FPGA) device, an application-specific integrated circuit (ASIC), a DSP, a controller, etc.), software (e.g., instructions executable by a processor), or any combination thereof.

In conjunction with the described aspects, an apparatus includes means for receiving a first user input corresponding to a user command to initiate a particular task, the first user input received via a first sensor. The means for receiving the first user input may include or correspond to the first sensor 110 or the second sensor 112 of FIG. 1, the third sensor 214 of FIG. 2, the microphone 638 or camera 650 of FIG. 6, one or more other structures or circuits configured to receive first user input, or any combination thereof.

The apparatus further includes means for receiving one or more subsequent user inputs, the one or more subsequent user inputs including a second user input received via a second sensor after the first user input is received. The means for means for receiving the one or more subsequent user inputs may include or correspond to the first sensor 110 or the second sensor 112 of FIG. 1, the third sensor 214 of FIG. 2, the microphone 638 or camera 650 of FIG. 6, one or more other structures or circuits configured to receive one or more subsequent user inputs, or any combination thereof.

The apparatus further includes means for initiating a remedial action in response to determining, based on a user experience evaluation unit, that the one or more subsequent user inputs correspond to a negative user experience. The means for initiating the remedial action may include or correspond to the processor 102 or the experience manager 124 of FIG. 1 or FIG. 2, the processor 610 of FIG. 6, one or more other structures or circuits configured to initiate a remedial action in response to determining, based on a user experience evaluation unit, that the one or more subsequent user inputs correspond to a negative user experience, or any combination thereof.

In a particular implementation, the apparatus includes means for determining that the one or more subsequent user inputs correspond to a negative user experience, such as the user experience evaluation module 132 of FIG. 1, FIG. 2, or FIG. 4, the processor 610 of FIG. 6, one or more other structures or circuits configured to determine that the one or more subsequent user inputs correspond to a negative user experience, or any combination thereof. In a particular implementation, the apparatus includes means for prompting the user for a non-audio input indicating a user-selected task to be associated with the user command, such as the voice interface 220, the speaker 238, the interface device 208, one or more other devices configured to prompt the user, or any combination thereof.

One or more of the disclosed aspects may be implemented in a system or an apparatus, such as the device 600, that may include a communications device, a fixed location data unit, a mobile location data unit, a mobile phone, a cellular phone, a satellite phone, a computer, a tablet, a portable computer, a display device, a media player, or a desktop computer. Alternatively or additionally, the device 600 may include a set top box, an entertainment unit, a navigation device, a personal digital assistant (PDA), a monitor, a computer monitor, a television, a tuner, a radio, a satellite radio, a music player, a digital music player, a portable music player, a video player, a digital video player, a digital video disc (DVD) player, a portable digital video player, a satellite, a vehicle, a component integrated within a vehicle, any other device that includes a processor or that stores or retrieves data or computer instructions, or a combination thereof. As another illustrative, non-limiting example, the device 600 may include remote units, such as hand-held personal communication systems (PCS) units, portable data units such as global positioning system (GPS) enabled devices, meter reading equipment, or any other device that includes a processor or that stores or retrieves data or computer instructions, or any combination thereof.

While FIG. 6 illustrates a wireless communication device including a processor configured to perform user experience evaluation, a processor configured to perform user experience evaluation may be included in various other electronic devices. For example, a processor configured to perform user experience evaluation as described with references to FIGS. 1-6, may be included in one or more components of a base station.

A base station may be part of a wireless communication system. The wireless communication system may include multiple base stations and multiple wireless devices. The wireless communication system may be a Long Term Evolution (LTE) system, a Code Division Multiple Access (CDMA) system, a Global System for Mobile Communications (GSM) system, a wireless local area network (WLAN) system, or some other wireless system. A CDMA system may implement Wideband CDMA (WCDMA), CDMA 1X, Evolution-Data Optimized (EVDO), Time Division Synchronous CDMA (TD-SCDMA), or some other version of CDMA.

Various functions may be performed by one or more components of the base station, such as sending and receiving messages and data (e.g., audio data). The one or more components of the base station may include a processor (e.g., a CPU), a transcoder, a memory, a network connection, a media gateway, a demodulator, a transmission data processor, a receiver data processor, a transmission multiple input-multiple output (MIMO) processor, transmitters and receivers (e.g., transceivers), an array of antennas, or a combination thereof. The base station, or one or more of the components of the base station, may include a processor configured to perform user experience evaluation, as described above with reference to FIGS. 1-6.

During operation of a base station, one or more antennas of the base station may receive a data stream from a wireless device. A transceiver may receive the data stream from the one or more antennas and may provide the data stream to the demodulator. The demodulator may demodulate modulated signals of the data stream and provide demodulated data to the receiver data processor. The receiver data processor may extract audio data from the demodulated data and provide the extracted audio data to the processor.

The processor may provide the audio data to the transcoder for transcoding. The decoder of the transcoder may decode the audio data from a first format into decoded audio data and the encoder may encode the decoded audio data into a second format. In some implementations, the encoder may encode the audio data using a higher data rate (e.g., upconvert) or a lower data rate (e.g., downconvert) than received from the wireless device. In other implementations the audio data may not be transcoded. Transcoding operations (e.g., decoding and encoding) may be performed by multiple components of the base station. For example, decoding may be performed by the receiver data processor and encoding may be performed by the transmission data processor. In other implementations, the processor may provide the audio data to the media gateway for conversion to another transmission protocol, coding scheme, or both. The media gateway may provide the converted data to another base station or core network via the network connection.

Although one or more of FIGS. 1-6 may illustrate systems, apparatuses, and/or methods according to the teachings of the disclosure, the disclosure is not limited to these illustrated systems, apparatuses, and/or methods. One or more functions or components of any of FIGS. 1-6 as illustrated or described herein may be combined with one or more other portions of another of FIGS. 1-6. For example, one or more elements of the method 300 of FIG. 3 may be performed in combination with one or more elements of the method 500 of FIG. 5 or other operations described herein. Accordingly, no single implementation described herein should be construed as limiting and implementations of the disclosure may be suitably combined without departing form the teachings of the disclosure. As an example, one or more operations described with reference to FIGS. 1-6 may be optional, may be performed at least partially concurrently, and/or may be performed in a different order than shown or described.

Those of skill would further appreciate that the various illustrative logical blocks, configurations, modules, circuits, and algorithm steps described in connection with the implementations disclosed herein may be implemented as electronic hardware, computer software executed by a processor, or combinations of both. Various illustrative components, blocks, configurations, modules, circuits, and steps have been described above generally in terms of their functionality. Whether such functionality is implemented as hardware or processor executable instructions depends upon the particular application and design constraints imposed on the overall system. Skilled artisans may implement the described functionality in varying ways for each particular application, but such implementation decisions should not be interpreted as causing a departure from the scope of the present disclosure.

The steps of a method or algorithm described in connection with the disclosure herein may be implemented directly in hardware, in a software module executed by a processor, or in a combination of the two. A software module may reside in random access memory (RAM), flash memory, read-only memory (ROM), programmable read-only memory (PROM), erasable programmable read-only memory (EPROM), electrically erasable programmable read-only memory (EEPROM), registers, hard disk, a removable disk, a compact disc read-only memory (CD-ROM), or any other form of non-transient storage medium known in the art. An exemplary storage medium is coupled to the processor such that the processor can read information from, and write information to, the storage medium. In the alternative, the storage medium may be integral to the processor. The processor and the storage medium may reside in an application-specific integrated circuit (ASIC). The ASIC may reside in a computing device or a user terminal. In the alternative, the processor and the storage medium may reside as discrete components in a computing device or user terminal.

The previous description is provided to enable a person skilled in the art to make or use the disclosed implementations. Various modifications to these implementations will be readily apparent to those skilled in the art, and the principles defined herein may be applied to other implementations without departing from the scope of the disclosure. Thus, the present disclosure is not intended to be limited to the implementations shown herein but is to be accorded the widest scope possible consistent with the principles and novel features as defined by the following claims.

What is claimed is:

1. A device comprising:
a memory configured to store a user experience evaluation unit; and
a processor coupled to the memory, the processor configured to:
receive a first user input corresponding to a user command to initiate a particular task, the first user input received via a first sensor;
initiate performance of the particular task in response to the first user input;
after initiation of performance of the particular task, receive one or more subsequent user inputs, the one or more subsequent user inputs including a second user input received via a second sensor and the one or more subsequent user inputs associated with user experience associated with the performance of the particular task; and
initiate a remedial action associated with the performance of the particular task in response to determining, based on evaluation of the one or more subsequent user inputs by the user experience evaluation unit, that the user experience associated with the performance of the particular task corresponds to a negative user experience.

2. The device of claim 1, further comprising:
a microphone; and
a camera, wherein the one or more subsequent user inputs include an audio input captured by the microphone, a video input captured by the camera, or a combination thereof.

3. The device of claim 2, wherein the first sensor includes the microphone and the second sensor includes the camera.

4. The device of claim 1, wherein the user experience evaluation unit is executable to perform at least one of: speech keyword detection, audio emotion analytics, video emotion analytics, prosody analytics, or audio event detection.

5. The device of claim 1, wherein the first user input includes an audio input of a user, wherein the memory is further configured to store a mapping unit that maps user commands to associated tasks, and wherein the processor is further configured to:
determine the user command based on the audio input; and
access the mapping unit using the user command to select the particular task.

6. The device of claim 5, wherein the remedial action includes prompting the user for a non-audio input indicating a user-selected task to be associated with the user command.

7. The device of claim 5, wherein the remedial action includes suggesting that the user perform one or more actions to enhance speech recognition of audio captured by a microphone.

8. The device of claim 1, wherein the remedial action includes at least one of: playing soothing music, adjusting a voice interface to speak in a calming manner, or recommending a relaxing activity for a user.

9. The device of claim 1, wherein the processor is implemented in a vehicle, wherein the remedial action includes prompting a user of the vehicle for information regarding the user experience, and wherein the processor is configured to delay performing the remedial action until the user is detected to have a non-negative user experience, the user has shut off the vehicle, or both.

10. A method comprising:
receiving, at a processor, a first user input corresponding to a user command to initiate a particular task, the first user input received via a first sensor;
initiating, at the processor, performance of the particular task in response to the first user input;
after initiation of performance of the particular task, receiving one or more subsequent user inputs, the one or more subsequent user inputs including a second user input received via a second sensor and the one or more subsequent user inputs associated with user experience associated with the performance of the particular task; and
initiating a remedial action associated with the performance of the particular task in response to determining, based on evaluation of the one or more subsequent user inputs by a user experience evaluation unit, that the user experience associated with the performance of the particular task corresponds to a negative user experience.

11. The method of claim 10, wherein the first sensor includes a microphone and the second sensor includes a camera.

12. The method of claim 10, wherein determining that the one or more subsequent user inputs correspond to a negative user experience includes performing at least one of speech keyword detection, audio emotion analytics, video emotion analytics, prosody analytics, or audio event detection.

13. The method of claim 10, wherein the first user input includes an audio input of a user, and further comprising:
   determining the user command based on the audio input; and
   selecting the particular task based on the user command.

14. The method of claim 13, wherein the remedial action includes prompting the user for a non-audio input indicating a user-selected task to be associated with the user command.

15. The method of claim 13, wherein the remedial action includes suggesting that the user close a window, direct speech toward a microphone, speak more loudly or distinctly, or a combination thereof.

16. The method of claim 10, wherein the remedial action includes at least one of: playing soothing music, adjusting a voice interface to generate speech to have a calming effect, or recommending a relaxing activity for a user.

17. The method of claim 10, wherein the remedial action includes prompting a user of a vehicle for information regarding the user experience, and wherein performance of the remedial action is delayed until the user is detected to have a non-negative user experience, the user has shut off the vehicle, or both.

18. A non-transitory computer-readable medium storing instructions that, when executed by a processor, cause the processor to initiate, perform, or control operations comprising:
   receiving a first user input corresponding to a user command to initiate a particular task, the first user input received via a first sensor;
   initiating performance of the particular task in response to the first user input;
   after initiation of performance of the particular task, receiving one or more subsequent user inputs, the one or more subsequent user inputs including a second user input received via a second sensor and the one or more subsequent user inputs associated with user experience associated with the performance of the particular task; and
   initiating a remedial action associated with the performance of the particular task in response to determining, based on evaluation of the one or more subsequent user inputs by a user experience evaluation unit, that the user experience associated with the performance of the particular task corresponds to a negative user experience.

19. The non-transitory computer-readable medium of claim 18, wherein the first sensor includes a microphone and the second sensor includes a camera.

20. The non-transitory computer-readable medium of claim 18, wherein determining that the one or subsequent user inputs correspond to a negative user experience includes performing at least one of audio emotion analytics or video emotion analytics.

21. The non-transitory computer-readable medium of claim 18, wherein the first user input includes an audio input of a user, and wherein the operations further comprise:
   determining the user command based on speech recognition of the audio input; and
   selecting the particular task based on the user command.

22. The non-transitory computer-readable medium of claim 21, wherein the remedial action includes prompting the user to perform one or more actions to enhance speech recognition of subsequent audio input.

23. The non-transitory computer-readable medium of claim 18, wherein the remedial action includes at least one of: playing soothing music, adjusting a voice interface to generate speech to have a calming effect, or recommending a relaxing activity for a user.

24. The non-transitory computer-readable medium of claim 18, wherein performance of the remedial action is delayed until the negative user experience is detected to have ended.

25. An apparatus comprising:
   means for receiving a first user input corresponding to a user command to initiate a particular task, the first user input received via a first sensor;
   means for initiating performance of the particular task in response to the first user input;
   means for receiving one or more subsequent user inputs, the one or more subsequent user inputs including a second user input received via a second sensor after the first user input is received, the one or more subsequent user inputs received after initiation of performance of the particular task, and the one or more subsequent user inputs associated with user experience associated with the performance of the particular task; and
   means for initiating a remedial action associated with the performance of the particular task in response to determining, based on evaluation of the one or more subsequent user inputs by a user experience evaluation unit, that the user experience associated with the performance of the particular task corresponds to a negative user experience.

26. The apparatus of claim 25, wherein the first sensor includes a microphone and the second sensor includes a camera.

27. The apparatus of claim 25, further comprising means for determining that the one or more subsequent user inputs correspond to a negative user experience.

28. The apparatus of claim 25, wherein the first user input includes an audio input of a user.

29. The apparatus of claim 28, further comprising means for prompting the user for a non-audio input indicating a user-selected task to be associated with the user command.

30. The apparatus of claim 25, wherein the remedial action includes at least one of: playing soothing music, adjusting a voice interface to generate speech to have a calming effect, or recommending a relaxing activity for a user.

* * * * *